(12) United States Patent
Liu et al.

(10) Patent No.: US 12,336,827 B2
(45) Date of Patent: Jun. 24, 2025

(54) CARDIAC TRANSMEMBRANE POTENTIAL RECONSTRUCTION METHOD BASED ON GRAPH CONVOLUTIONAL NEURAL NETWORK AND ITERATIVE THRESHOLD CONTRACTION ALGORITHM

(71) Applicant: ZHEJIANG UNIVERSITY, Zhejiang (CN)

(72) Inventors: Huafeng Liu, Hangzhou (CN); Lide Mu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 614 days.

(21) Appl. No.: 17/625,766

(22) PCT Filed: Aug. 19, 2021

(86) PCT No.: PCT/CN2021/113447
§ 371 (c)(1),
(2) Date: Jan. 9, 2022

(87) PCT Pub. No.: WO2022/262109
PCT Pub. Date: Dec. 22, 2022

(65) Prior Publication Data
US 2023/0263450 A1  Aug. 24, 2023

(30) Foreign Application Priority Data
Jun. 18, 2021  (CN) .......................... 202110682912.1

(51) Int. Cl.
*A61B 5/318*  (2021.01)
*G16H 50/50*  (2018.01)

(52) U.S. Cl.
CPC ............. *A61B 5/318* (2021.01); *G16H 50/50* (2018.01); *A61B 2576/023* (2013.01)

(58) Field of Classification Search
None
See application file for complete search history.

(56) References Cited

PUBLICATIONS

Non-invasive Reconstruction of Dynamic Myocardial Transmembrane Potential with Graph-based Total Variation Constraints. Xie et al. (Year: 2019).*

* cited by examiner

*Primary Examiner* — Delomia L Gilliard
(74) *Attorney, Agent, or Firm* — Jiwen Chen; Joywin IP Law PLLC

(57) ABSTRACT

The present invention discloses a cardiac transmembrane potential reconstruction method based on a graph convolutional neural network and an iterative threshold contraction algorithm. The cardiac transmembrane potential is econstructed iteratively through the iterative threshold contraction algorithm embedded in the graph convolutional neural network, and the graph convolutional neural network is used to extract the correlation information between nodes in the non-Euclidean dat a of the cardiac transmembrane potential, while retaining the rigorous mathematical calculations of the iterative threshold contraction algorithm, a solution og the cardiac transmembrane potential is obtained after multiple iterations. Based on the reconstructed temporal and spatial sequence of the cardiac transmembrane potential, the present invention can assist in the diagnosis of common heart diseases such as premature ventricular beats, tachycardia, atrial fibrillation, myocardial ischemia and myocardial infarction in arrhythmia, and is useful for subsequent treatment and provide guidance for radiofrequency ablation surgery.

7 Claims, 5 Drawing Sheets

CARDIAC TRANSMEMBRANE POTENTIAL RECONSTRUCTION METHOD BASED ON GRAPH CONVOLUTIONAL NEURAL NETWORK AND ITERATIVE THRESHOLD CONTRACTION ALGORITHM

This is a U.S. national stage application of PCT Application No. PCT/CN2021/113447 under 35 U.S.C. 371, filed Aug. 19, 2021 in Chinese, claiming priority to Chinese Patent Applications No. 202110682912.1, filed Jun. 18, 2021, all of which are hereby incorporated by reference.

FIELD OF TECHNOLOGY

The present invention belongs to a technical field of cardiac transmembrane potential reconstruction, and specifically relates to a cardiac transmembrane potential reconstruction method based on graph convolutional neural networks and an iterative threshold contraction algorithm.

BACKGROUND TECHNOLOGY

Disturbance of normal heart rhythm, called arrhythmia, has become one of the diseases with the highest incidence and fatality rate in the world. Because arrhythmia often causes changes in the mechanical movement of the myocardium, arrhythmia has also become ventricular premature beats and hypercardiac has become the primary cause of heart disease such as rapid, atrial fibrillation, premature atrial, myocardial ischemia, myocardial infarction, and sudden cardiac death. According to the statistics of the World Health Organization, more than 10 million people die from arrhythmia diseases in the world every year, and more people become disabled due to arrhythmia diseases. Although the incidence of arrhythmia diseases in our country is relatively low, it is due to the huge population base, more than 800,000 people still die from this disease every year. Therefore, accurately identifying at-risk patients and providing accurate diagnosis and guiding treatment are of great clinical significance for reducing the fatality rate of such diseases and improving the cure rate.

Since the electrocardiogram signal that can be measured on the body surface is a mapping of the surface potential of the heart, in recent years, some researchers have also proposed the technique of electrocardiographic imaging (ECGI). This method mainly uses the multi-lead ECG measured on the body surface. Signals (generally more than 64 electrodes) and the geometric model of the heart and torso are reconstructed to obtain the electrophysiological activity information of the heart surface, including the cardiac transmembrane potential, the extracellular potential of the heart endocardium and epicardium, and the activation sequence of the heart surface. Compared with the most accurate clinically invasive methods, ECGI technology can be used to non-invasively record the electrophysiological activities of the heart, screen and identify high-risk patients with arrhythmia and sudden cardiac death, and provide actual spatial heterogeneity information in the heart for diagnosis and locating arrhythmia diseases.

Therefore, if the accuracy of the reconstruction of the cardiac surface potential can be improved, and the complexity and calculation time of the algorithm can be reduced, it is of great significance for the diagnosis and treatment of clinical arrhythmia and some cardiac ischemic diseases.

SUMMARY OF THE INVENTION

In view of the above, the present invention provides a cardiac transmembrane potential reconstruction method based on graph convolutional neural network and iterative threshold contraction algorithm. On the basis of retaining the rigorous mathematical reasoning of traditional iterative threshold contraction algorithm, it makes full use of graph convolutional neural network's feature of interconnection between nodes based on cardiac extracellular potential datas based on the graph, the temporal and spatial distribution of the cardiac transmembrane potential can be reconstructed through the multi-lead ECG data measured on the body surface, so as to diagnose some heart diseases.

A cardiac transmembrane potential reconstruction method based on graph convolutional neural network and iterative threshold contraction algorithm, comprising the following steps:

(1) performing enhanced CT plain scan on the patient's torso, and acquiring enhanced CT slice images of the patient's thoracic cavity; (2) establishing a finite element model of a heart surface and a torso surface according to the enhanced CT slice images, and finding the positive relationship between a body surface potential and a cardiac transmembrane potential, that is, $\Phi = HU$, wherein $\Phi$ is the body surface potential and U is the cardiac transmembrane potential, H represents the forward conversion matrix between H and $\Phi$;

(3) collecting the patient's multi-lead body surface ECG signal $\Phi$, and filtering the ECG signal;

(4) according to the obtained $\Phi$ and H, initializing the cardiac transmembrane potential signal;

(5) according to an initial value of the cardiac transmembrane potential signal, the cardiac transmembrane potential is reconstructed by an iterative threshold contraction algorithm of embedded a graph convolutional neural network.

Further, in the step (1), a scope of the CT plain scan needs to include the entire thoracic cavity, at the same time, a spatial geometric positions of the heart and thoracic cavity and a position of the electrodes in the multi-lead ECG of the surface of the thoracic cavity are recorded at the same time.

Further, a specific implementation of the step (2) is: first the multiple axially enhanced CT slice images of the thoracic cavity are segmented to a left ventricle endocardium, a right ventricle endocardium and a epicardium by using a Matlab software, and a 3D Slicer software is used to mark a position of a multi-lead electrode on the enhanced CT slice image. Further through a finite element method, a finite element model of the heart surface and the torso surface can be obtained and registered. Then based on the finite element model of heart surface and the torso surface and then through a boundary element method, the positive relationship $\Phi = HU$ of the heart transmembrane potential propagating to the thoracic cavity surface can be obtained.

Further, in the step (3), the patient is made to wear a body surface potential detection device with 64-lead electrodes distributed for measurement, and the patient's 64-lead body surface ECG signal is collected and obtained, and the 64-lead body surface ECG signal is processed by wavelet transform to flatten and denoise the signal.

Further, a formula for initializing the cardiac transmembrane potential signal in the step (4) is as follows:

$$u^{(0)} = Q_{init}\Phi$$

$$Q_{init} = \arg\min_{Q} \|Q\Phi - U\|_F^2 = U\Phi^T(\Phi\Phi^T)^{-1}$$

wherein, $u_{(0)}$ is a initial value of the cardiac transmembrane potential signal, $\|\ \|_F$ represents a F norm, T represents a transposition, and Q represents a reverse conversion matrix between Φ and U.

Further, the specific implementation of the step (5) is as follows:

5.1 mapping update steps in ISTA to a graph convolutional neural network model composed of a fixed number of block cascades, and each block corresponds to an iteration in ISTA;

5.2 a regularization matrix in a L1 norm regularization is replaced to a nonlinear transformation function corresponding to a block, the following objective reconstruction equation is established:

$$\min_U \frac{1}{2}\|HU - \Phi\|_2^2 + \lambda\|\Gamma(U)\|_1$$

wherein, $\|\ \|_2$ represents a 2 norm, $\|\ \|_1$ represents a 1 norm, λ is aregularization coefficient, and Γ( ) is the nonlinear transformation function corresponding to ablock;

5.3 the above-mentioned objective reconstruction equation is optimized by using ISTA, each iteration in ISTA is divided into two steps: the first step is gradient descent, and the second step is to solve a near-end operator;

5.4 the graph convolutional neural network model based on ISTA is trained by using existing data samples, and finally using the trained network model to solve a ECG inverse problem, so as to complete the reconstruction of the cardiac transmembrane potential.

Further, the block in step 5.1 is to use a general nonlinear transformation function to sparse U, and its specific structure is from input to output, it is composed of graph convolutional layer G1, ReLU activation function R1, graph convolutional layer G2, soft threshold shrinkage operator, graph convolutional layer G3, ReLU activation function R2, graph convolutional layer G4 and connected in sequence.

Further, the expression of the gradient descent step in the step 5.3 is as follows:

$$\tilde{U}^{(k)} = U^{(k-1)} - t^{(k)}H^T(HU^{(k-1)} - \Phi)$$

wherein, t represents a step size, T represents a transposition, the superscripts k and k-1 represent a number of iterations, and k is a natural number greater than 0, and $\tilde{U}$ is a intermediate variable about U obtained by gradient descent.

Further, the expression of solving a near-end operator in the step 5.3 is as follows:

$$U^{(k)} = \arg\min_U \frac{1}{2}\left\|U - \tilde{U}^{(k)}\right\|_2^2 + \lambda\|\Gamma(U)\|_1$$

wherein, $\tilde{U}$ is a intermediate variable about U obtained by gradient descent, the superscript k represents A number of iterations, and k is a natural number greater than 0.

Further, a implementation of the graph convolutional layer satisfies the following hierarchical propagation rule:

$$G^{(l+1)} = \sigma\left(\tilde{D}^{-\frac{1}{2}}\tilde{A}\tilde{D}^{-\frac{1}{2}}G^{(l)}W^{(l)}\right)$$

wherein, $\tilde{A} = A + I_N$, A is a adjacency matrix of the self-connected undirected graph, $I_N$ is a identity matrix, $\tilde{D}$ is a degree matrix and the diagonal element value is $$\tilde{D}_{ii} = \sum_j \tilde{A}_{ij},$$

$\tilde{A}_{ij}$ is a element value in the i-th row and j-th column, superscripts l and l+1 represent a sequence number of the graph convolutional layer, G represents the output of the graph convolutional layer, W is a weight matrix in the graph convolutional layer, and σ( ) represents a ReLU activation function.

The present invention uses the iterative threshold contraction algorithm embedded in the graph convolutional neural network to iteratively reconstruct the cardiac transmembrane potential, and uses the graph convolutional neural network to extract the correlation information between nodes in the non-Euclidean data of the heart transmembrane potential, while retaining the rigorous mathematical calculation of the iterative threshold shrinkage algorithm, after multiple iterations, obtains the solution of the cardiac transmembrane potential. The present invention can assist in the diagnosis of common heart diseases such as ventricular premature beats, tachycardia, atrial fibrillation, myocardial ischemia and myocardial infarction in arrhythmia based on the reconstructed temporal and spatial sequence of cardiac transmembrane potentials, and is useful for subsequent treatment and provide guidance for radiofrequency ablation surgery.

DESCRIPTION OF THE EMBODIMENTS

In order to describe the present invention in more detail, the technical solution of the present invention will be described in detail below with reference to the accompanying drawings and specific embodiments.

The cardiac transmembrane potential reconstruction method based on graph convolutional neural network and iterative threshold contraction algorithm of the present invention, comprising the following steps:

(1) performing enhanced CT plain scan on the patient's torso

A scope of the CT plain scan needed to include the entire thoracic cavity, at the same time, a spatial geometric positions of the heart and thoracic cavity and a position of the electrodes in the multi-lead ECG of the surface of the thoracic cavity were recorded at the same time.

(2) establishing a finite element model of a heart surface and a torso surface according to the enhanced CT slice images, and finding the positive relationship between a body surface potential and a cardiac transmembrane potential: Φ=HU.

First, the multiple axially enhanced CT slice images of the thoracic cavity were segmented to a left ventricle endocardium, a right ventricle endocardium and a epicardium by using a Matlab software, and a 3D Slicer software was used to mark a position of a multi-lead electrode on the enhanced CT slice image. Further through a finite element method, a finite element model of the heart surface and the torso surface could be obtained and registered. Then based on the finite element model of heart surface and the torso surface and then through a boundary element method, the positive relationship Φ=HU of the heart transmembrane potential propagating to the thoracic cavity surface could be obtained.

(3) collecting the patient's 64-lead body surface ECG signal, and filtering the ECG signal 64-lead electrodes were placed on a surface of the patient's chest cavity to measure the ECG signal on the torso surface, and the measured 64-lead ECG signal was further flattened and denoised by wavelet transform.

(4) according to the obtained Φ and H, initializing the cardiac transmembrane potential signal. A formula for initializing the cardiac transmembrane potential signal is as follows:

$$u^{(0)} = Q_{init}\Phi$$

$$Q_{init} = \arg\min_{Q}\|Q\Phi - U\|_F^2 = U\Phi^T(\Phi\Phi^T)^{-1}$$

wherein, $u^{(0)}$ is a initial value of the cardiac transmembrane potential signal, $\|\ \|_F$ represents a F norm, T represents a transposition, and Q represents a reverse conversion matrix between Φ and U.

(5) according to the initial value of the cardiac transmembrane potential signal, the cardiac transmembrane potential was reconstructed by an iterative threshold contraction algorithm of embedded a graph convolutional neural network.

Figure 1:
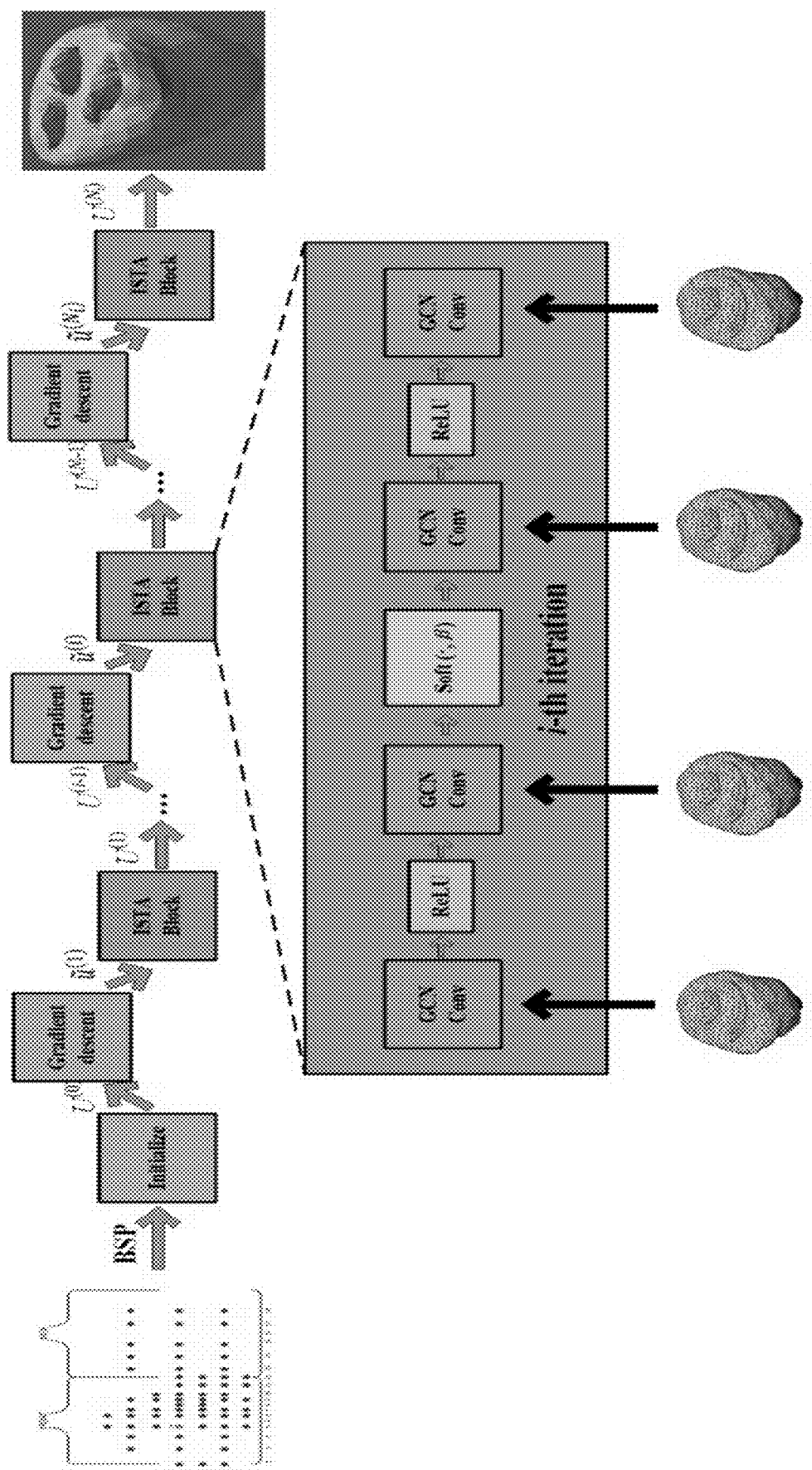
FIG. 1 is a schematic flow chart of the iterative threshold shrinkage algorithm based on the embedding graph convolutional neural network of the present invention.

As shown in FIG. 1, the present invention used graph convolutional neural network to improve the traditional iterative threshold shrinkage algorithm ISTA, the update steps in ISTA were mapped to a raph convolutional neural network model composed of a fixed number of stages, that is, using a general nonlinear transformation function to sparse U, which could be expressed specifically four graph convolutional layers and ReLU activation function.

First, a regularization matrix in a L1 norm regularization was replaced to the above nonlinear transformation function, which can be expressed as:

$$\min_{X} \frac{1}{2}\|HU_{TMP} - \Phi\|_2^2 + \lambda\|\Gamma(U_{TMP})\|_1$$

Then, the ISTA algorithm was used to solve the above-mentioned constraint minimization problem, each iteration in ISTA was divided into two steps: the first step was gradient descent, and the second step was to solve a near-end operator. In ISTA-Net, the steps of retaining the first gradient descent were as follows:

$$\tilde{U}_{TMP}^{(i)} = U_{TMP}^{(i-1)} - t^{(i)}H \cdot (HU_{TMP}^{(i-1)} - \Phi)$$

For the second step of solving the near-end operator shown in the following formula, only the step of soft threshold shrinkage calculation was retained. Before and after the soft threshold shrinkage, several convolutional layers and ReLU activation functions were used to replace the traditional algorithm. The calculation steps of the regularization matrix:

$$U_{TMP}^{(i)} = \arg\min_{X} \frac{1}{2}\|U_{TMP} - \tilde{U}_{TMP}^{(i)}\|_2^2 + \lambda\|\Gamma(U_{TMP})\|_1$$

Finally, ISTA-Net was trained through paired data, and then the trained model was used to solve the inverse problem. The implementation of graph convolution satisfies the hierarchical propagation rule shown in the following formula:

$$H^{(l+1)} = \sigma\left(\tilde{D}^{-\frac{1}{2}}\tilde{A}\tilde{D}^{-\frac{1}{2}}H^{(l)}W^{(l)}\right)$$

wherein, $\tilde{A}=A+I_N$, A was a adjacency matrix of the self-connected undirected graph, $I_N$ was a identity matrix, $$\tilde{D}_{ii} = \sum_{j}\tilde{A}_{ij}$$

and $W^{(l)}$ was a unique trainable weight matrix for each graph convolutional layer, that is a main parameter in the network. σ( ) was a ReLU activation function for each layer, for example, ReLU (·)=max(0, ·), etc. $H^{(l)} \in \square^{N \times D}$ was an activation matrix of the lth layer, that is, a output result of this layer, $H^{(0)}=X$, an input data was the activation value of 0th layer.

In the following specific experiments, we tested the entire algorithm of the present invention in a Windows 10 (64-bit) system, where the CPU was Intel® Core™ i9-7900x CPU @ 3.30 GHz 3.31 GHz, a the host memory is 32 GB RAM, the graphics card model was NVIDIA GeForce GTX 2080Ti, and the main programming environment was python 3.8.

Figure 2:
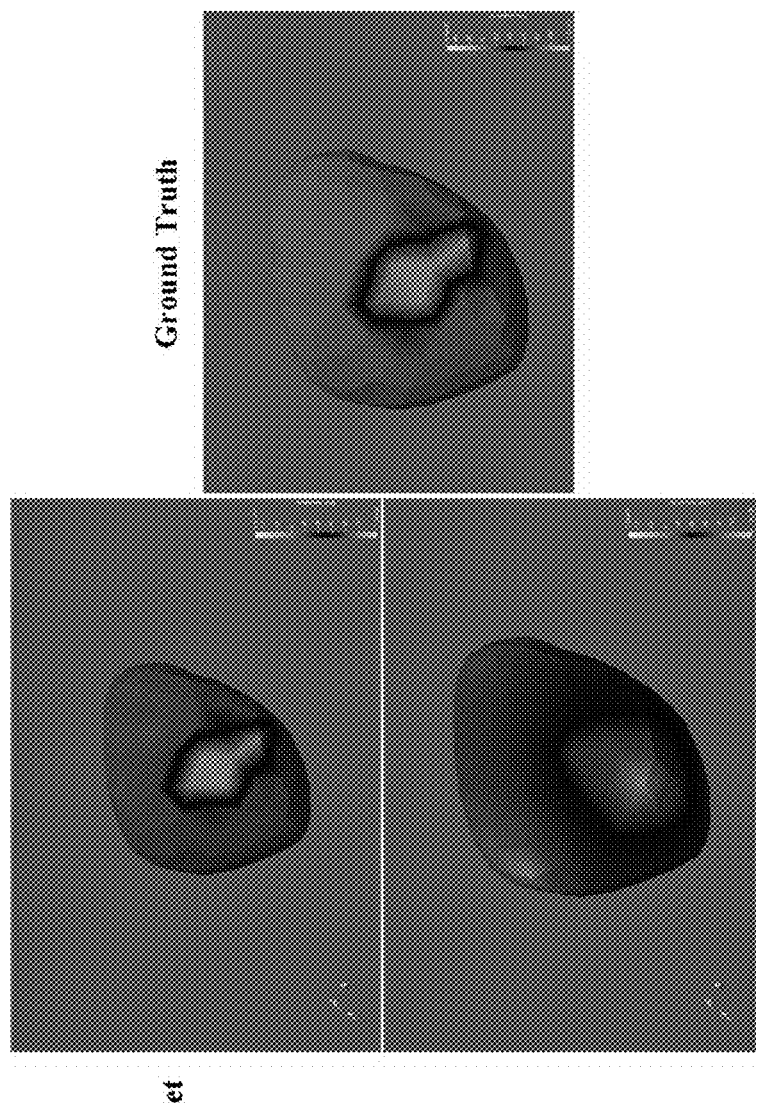
FIG. 2 is a spatial comparison result diagram of cardiac transmembrane potential reconstruction for ventricular premature beat data by the present invention and the existing TV algorithm.
Figure 3:
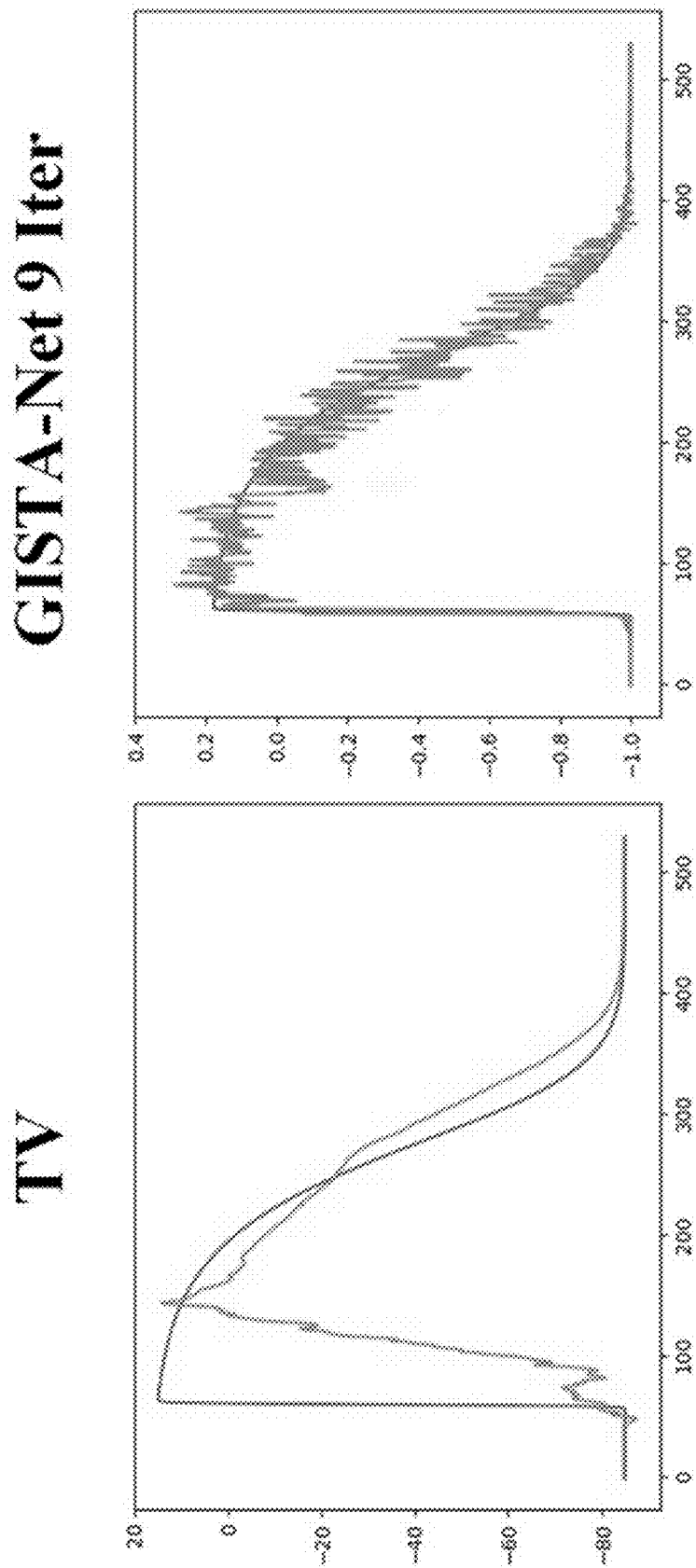
FIG. 3 is a time comparison result diagram of cardiac transmembrane potential reconstruction for ventricular premature beat data between the present invention and the existing TV algorithm.
Figure 4:
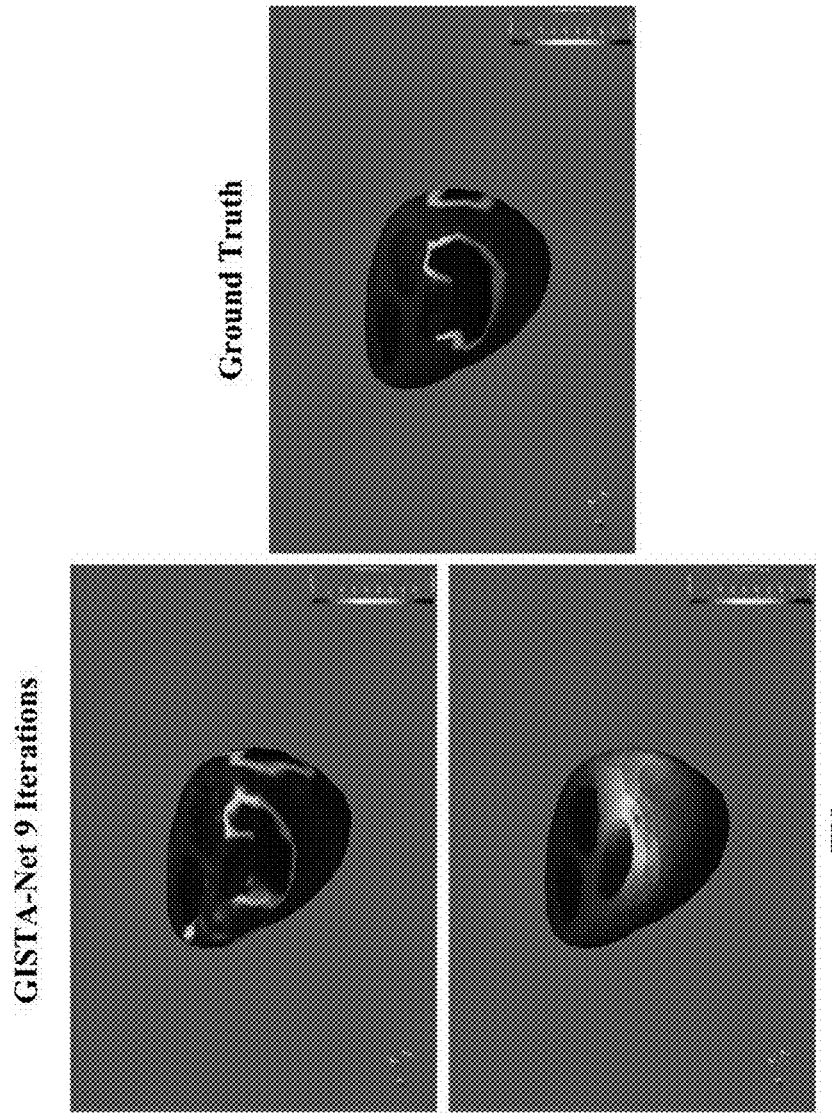
FIG. 4 is a diagram showing the spatial comparison result of reconstruction of cardiac transmembrane potential for myocardial infarction data between the present invention and the existing TV algorithm.
Figure 5:
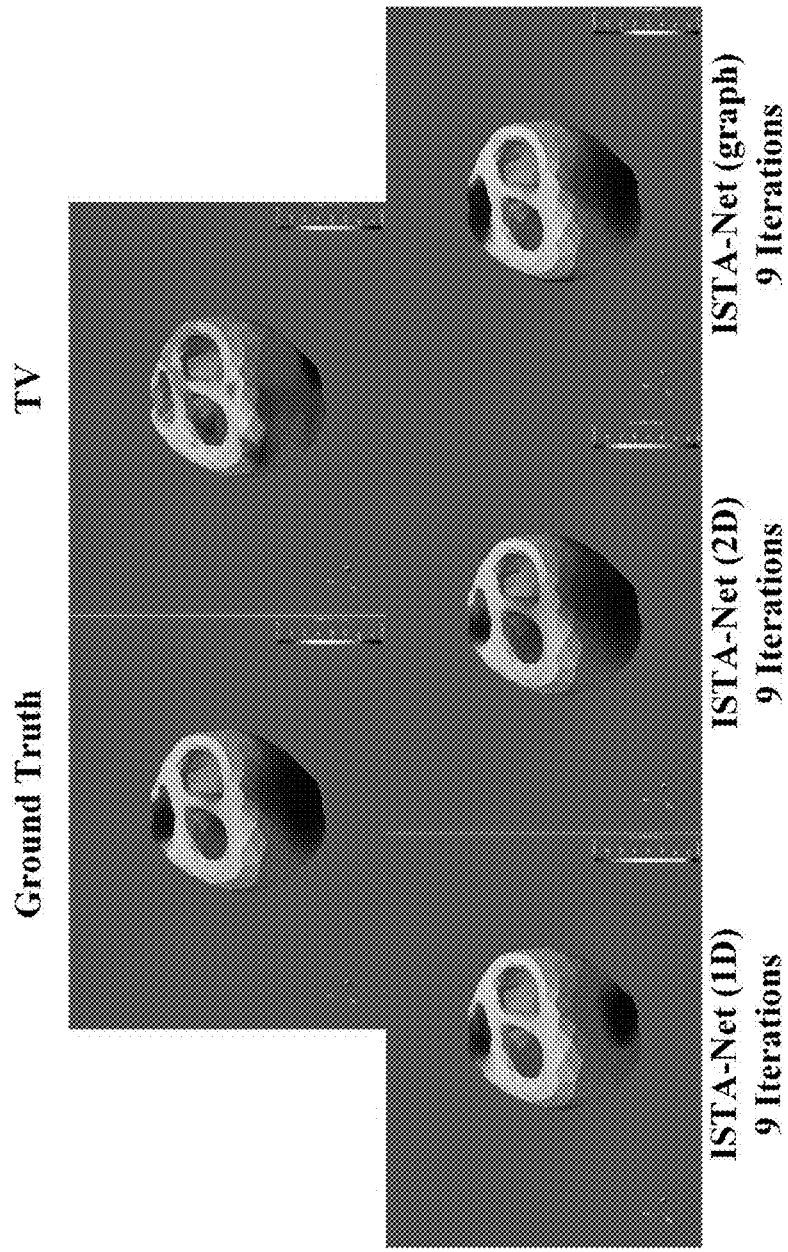
FIG. 5 is a spatial comparison result diagram of the cardiac activation time sequence reconstruction for myocardial infarction data between the present invention and the existing TV algorithm.

In order to verify the accuracy of the reconstruction of cardiac transmembrane potential and the diagnostic accuracy of cardiac diseases according to the present invention, we applied the above method to the data of ventricular premature beats and myocardial infarction to reconstruct the cardiac transmembrane potential. FIG. 2 showed the spatial comparison result of cardiac transmembrane potential reconstruction for ventricular premature beat data between the method of the present invention and the existing TV algorithm. From the reconstruction result of the present invention, the location of the occurrence of ventricular premature beats can be clearly seen. FIG. 3 showed the time comparison results of cardiac transmembrane potential reconstruction for ventricular premature beat data between the method of the present invention and the existing TV algorithm, and FIG. 4 showed the method of the present invention and the existing TV algorithm for cardiac transmembrane data of myocardial infarction. From the spatial comparison result of the potential reconstruction, the loca-

The invention claimed is:

1. A cardiac transmembrane potential reconstruction method based on graph convolutional neural network and iterative threshold contraction algorithm, comprising the following steps:

(1) performing enhanced CT plain scan on the patient's torso, and acquiring enhanced CT slice images of the patient's thoracic cavity;

(2) establishing a finite element model of a heart surface and a torso surface according to the enhanced CT slice images, and finding the positive relationship between a body surface potential and a cardiac transmembrane potential, that is, Φ=HU, where Φ is the body surface potential and U is the cardiac transmembrane potential, H represents the forward conversion matrix between H and Φ;

(3) collecting the patient's multi-lead body surface ECG signal Φ, and filtering the ECG signal;

(4) according to the obtained Φ and H, initializing the cardiac transmembrane potential signal;

(5) according to an initial value of the cardiac transmembrane potential signal, the cardiac transmembrane potential is reconstructed by an iterative threshold contraction algorithm of embedded a graph convolutional neural network;

wherein, in the step (3), the patient is made to wear a body surface potential detection device with 64-lead electrodes distributed for measurement, and the patient's 64-lead body surface ECG signal is collected and obtained, and the 64-lead body surface ECG signal is processed by wavelet transform to flatten and denoise the signal;

wherein, a formula for initializing the cardiac transmembrane potential signal in the step (4) is as follows:

$$u^{(0)} = Q_{init}\Phi$$

$$Q_{init} = \arg\min_{Q}\|Q\Phi - U\|_F^2 = U\Phi^T(\Phi\Phi^T)^{-1}$$

wherein, $u^{(0)}$ is a initial value of the cardiac transmembrane potential signal, $\|\ \|_F$ represents a F norm, T represents a transposition, and Q represents a reverse conversion matrix between Φ and U, wherein, the specific implementation of the step (5) is as follows:

(5.1) mapping update steps in ISTA to a graph convolutional neural network model composed of a fixed number of block cascades, and each block corresponds to an iteration in ISTA;

(5.2) replacing a regularization matrix in a L1 norm regularization with a nonlinear transformation function corresponding to a block, the following objective reconstruction equation is established:

$$\min_{U} \frac{1}{2}\|HU - \Phi\|_2^2 + \lambda\|\Gamma(U)\|_1$$

wherein, $\|\ \|_2$ represents a 2 norm, $\|\ \|_1$ represents a 1 norm, λ is a regularization coefficient, and Γ( ) is the nonlinear transformation function corresponding to a block;

(5.3) optimizing the above-mentioned objective reconstruction equation by using ISTA, each iteration in ISTA is divided into two steps: the first step is gradient descent, and the second step is to solve a near-end operator;

(5.4) training the graph convolutional neural network model based on ISTA by using existing data samples, and finally using the trained network model to solve a ECG inverse problem, so as to complete the reconstruction of the cardiac transmembrane potential.

2. The cardiac transmembrane potential reconstruction method according to claim 1, wherein, in the step (1), a scope of the CT plain scan needs to include the entire thoracic cavity, at the same time, a spatial geometric positions of the heart and thoracic cavity and a position of the electrodes in the multi-lead ECG of the surface of the thoracic cavity are recorded at the same time.

3. The cardiac transmembrane potential reconstruction method according to claim 1, wherein, a specific implementation of the step (2) is: first the multiple axially enhanced CT slice images of the thoracic cavity are segmented to a left ventricle endocardium, a right ventricle endocardium and a epicardium by using a Matlab software, and a 3D Slicer software is used to mark a position of a multi-lead electrode on the enhanced CT slice image, Further through a finite element method, a finite element model of the heart surface and the torso surface can be obtained and registered; then based on the finite element model of heart surface and the torso surface and then through a boundary element method, the positive relationship Ω=HU of the heart transmembrane potential propagating to the thoracic cavity surface is obtained.

4. The cardiac transmembrane potential reconstruction method according to claim 1, wherein, the block in step 5.1 is to use a general nonlinear transformation function to sparse U, and its specific structure is from input to output, it is composed of graph convolutional layer G1, ReLU activation function R1, graph convolutional layer G2, soft threshold shrinkage operator, graph convolutional layer G3, ReLU activation function R2, graph convolutional layer G4 and connected in sequence.

5. The cardiac transmembrane potential reconstruction method according to claim 4, wherein, a implementation of the graph convolutional layer satisfies the following hierarchical propagation rule:

$$G^{(l+1)} = \sigma\left(\tilde{D}^{-\frac{1}{2}}\tilde{A}\tilde{D}^{-\frac{1}{2}}G^{(l)}W^{(l)}\right)$$

wherein, $\tilde{A}=A+I_N$, A is a adjacency matrix of the self-connected undirected graph, $I_N$ is a identity matrix, $\tilde{D}$ is a degree matrix and the diagonal element value is $$\tilde{D}_{ii} = \sum_j \tilde{A}_{ij},$$

$A_{ij}$ is a element value in the i-th row and j-th column, superscripts l and l+1 represent a sequence number of the graph convolutional layer, G represents the output of the graph convolutional layer, W is a weight matrix in the graph convolutional layer, and σ( ) represents a ReLU activation function.

6. The cardiac transmembrane potential reconstruction method according to claim 1, wherein, the expression of the gradient descent step in the step 5.3 is as follows:

$$\tilde{U}^{(k)} = U^{(k-1)} - t^{(k)} H^T (HU^{(k-1)} - \Phi)$$

wherein, t represents a step size, T represents a transposition, the superscripts k and k-1 represent a number of iterations, and k is a natural number greater than 0, and Ũ is a intermediate variable about U obtained by gradient descent.

7. The cardiac transmembrane potential reconstruction method according to claim 1, wherein, the expression of solving a near-end operator in the step 5.3 is as follows:

$$U^{(k)} = \arg\min_U \frac{1}{2} \left\| U - \tilde{U}^{(k)} \right\|_2^2 + \lambda \|\Gamma(U)\|_1$$

wherein, Ũ is a intermediate variable about U obtained by gradient descent, the superscript k represents A number of iterations, and k is a natural number greater than 0.

* * * * *